United States Patent
Ebert et al.

(10) Patent No.: US 8,783,163 B2
(45) Date of Patent: Jul. 22, 2014

(54) PISTON PUMP DEVICE

(75) Inventors: Manuel Ebert, Luzern (CH); David Imboden, Baar (CH); Ivo Ramella, Ebikon (CH)

(73) Assignee: Madela Holding AG, Baar (CH)

( * ) Notice: Subject to any disclaimer, the term of this patent is extended or adjusted under 35 U.S.C. 154(b) by 747 days.

(21) Appl. No.: 13/070,921

(22) Filed: Mar. 24, 2011

(65) Prior Publication Data

US 2011/0296983 A1    Dec. 8, 2011

(30) Foreign Application Priority Data

Jun. 3, 2010 (CH) ..................................... 0886/10

(51) Int. Cl.
| | |
|---|---|
| *F04B 39/12* | (2006.01) |
| *F04B 53/16* | (2006.01) |
| *A61M 1/00* | (2006.01) |
| *F04B 27/08* | (2006.01) |
| *F04B 1/20* | (2006.01) |
| *F04B 27/00* | (2006.01) |
| *F04B 1/00* | (2006.01) |

(52) U.S. Cl.
CPC .............. *F04B 39/127* (2013.01); *F04B 53/16* (2013.01); *A61M 1/0066* (2013.01); *F04B 27/0856* (2013.01); *A61M 1/0068* (2013.01); *F04B 1/2071* (2013.01); *F04B 27/00* (2013.01); *F04B 1/00* (2013.01)
USPC .............................. 92/118; 417/464; 604/317

(58) Field of Classification Search
CPC .... A61M 1/00; F04B 39/0044; F04B 1/2071; F04B 53/16; F16F 15/06
USPC ............ 92/117 R, 118, 146, 161, 169.1, 187; 417/464; 604/317
See application file for complete search history.

(56) References Cited

U.S. PATENT DOCUMENTS

| | | | | |
|---|---|---|---|---|
| 300,400 | A | * | 6/1884 | Shepard .......................... 417/464 |
| 556,704 | A | * | 3/1896 | Stevens .......................... 417/464 |
| 2,240,121 | A | * | 4/1941 | Patterson ....................... 417/454 |
| 2,872,101 | A | * | 2/1959 | Ryba .............................. 417/418 |

(Continued)

FOREIGN PATENT DOCUMENTS

| | | |
|---|---|---|
| EP | 0791366 | 8/1997 |
| WO | 95/33924 | 12/1995 |

OTHER PUBLICATIONS

International Search Report for PCT App. No. PCT/CH2011/000126, dated Aug. 22, 2011.
International Search Report for Swiss Patent App. No. 0886/10 dated Aug. 17, 2010.

*Primary Examiner* — Thomas E Lazo
(74) *Attorney, Agent, or Firm* — McDonnell Boehnen Hulbert & Berghoff LLP

(57) ABSTRACT

A piston pump device has a support unit, a pump cylinder, and a pump piston arranged in the pump cylinder. The pump cylinder has a longitudinal center axis, and a cylinder bottom arranged perpendicular to the longitudinal center axis. The pump piston is movable relative to the cylinder bottom, and the pump cylinder is secured on the support unit by a securing unit. The securing unit has a leaf spring, which permits a pivoting movement of the longitudinal center axis of the pump cylinder relative to the support unit. The piston pump device is wear-resistant and runs quietly. When used as a suction pump, the piston pump device additionally permits a controllable air flow until the pump comes to a stop.

17 Claims, 3 Drawing Sheets

(56) References Cited

U.S. PATENT DOCUMENTS

| | | | |
|---|---|---|---|
| 3,738,232 A * | 6/1973 | Kado | 92/161 |
| 4,161,812 A * | 7/1979 | Litch, III | 29/446 |
| 4,451,211 A * | 5/1984 | Schonwald | 417/271 |
| 6,450,777 B2 * | 9/2002 | Lynn et al. | 417/269 |
| 6,742,998 B2 * | 6/2004 | Kawahara et al. | 417/416 |
| 2001/0014288 A1 * | 8/2001 | Lynn et al. | 417/269 |
| 2003/0017064 A1 | 1/2003 | Kawahara et al. | |

* cited by examiner

US 8,783,163 B2

PISTON PUMP DEVICE

CROSS REFERENCE TO RELATED APPLICATIONS

The present application claims priority to Swiss Patent Application No. 0886/10 filed Jun. 3, 2010, the entire contents of which are incorporated herein by reference.

TECHNICAL FIELD

The present invention relates to a piston pump device. This pump device is suitable in particular as a suction pump or vacuum pump, particularly in the medical sector. Preferred areas of use are drainage pumps for aspiration of body fluids.

BACKGROUND

Piston pumps with pump cylinder and pump piston are well known from different areas of use. For example, the applicant has for some years been selling a drainage pump with the name Dominant 35c/i, which has two double-action piston/cylinder systems working in opposite directions.

Other piston pumps are described in WO 95/33924 and in EP 0 791 366, for example.

Piston pumps are exposed to forces that adversely affect their smooth running Various types of bearings, in particular roller bearings and sliding bearings, are used to support individual parts of the pump. However, these bearings are subject to wear. For example, sliding bearings or grooved ball bearings are always loaded on the same side. This leads to knocking noises. As a consequence, the bearings have to be replaced after a certain length of time. Conventional grooved ball bearings also require a certain speed of rotation in order to build up a lubricating film. If the pivoting speed of the pump cylinder is relatively low, the lubricating action is unsatisfactory. This is especially problematic in suction pumps with adjustable or controllable air flow since the pivoting speed of the cylinder also decreases when there is a reduction in the air flow.

SUMMARY

It is an object of the invention to make available a piston pump, in particular for suction pumps in the medical sector, which piston pump is subject to the least possible wear and runs very smoothly.

The piston pump device according to the invention has a support unit, a pump cylinder, and a pump piston arranged in the pump cylinder. The pump cylinder has a longitudinal center axis, and a cylinder bottom arranged perpendicular to the longitudinal center axis. The pump piston is movable relative to this cylinder bottom, and the pump cylinder is secured on the support unit by a securing unit. According to the invention, the securing unit has a leaf spring, which permits a pivoting movement of the pump cylinder, or of the longitudinal center axis of the pump cylinder, relative to the support unit. The securing device can be secured on the jacket of the pump cylinder. However, it is preferably secured on the cylinder bottom.

Leaf springs have the advantage that, with slight deflection, they are practically free from wear. Since the pump cylinder executes only relatively small pivoting movements, a small angle of deflection of the leaf spring lying within the elastic range of the spring is ensured.

The piston pump device according to the invention not only has a wear-resistant bearing, it also reduces the manufacturing costs, since roller bearings and slide bearings can be omitted. Moreover, the reduction in the number of movable parts simplifies production and also maintenance and permits a compact structure.

The piston pump device can be used in particular in a suction pump. By virtue of the use of at least one leaf spring as a bearing, the air flow of the suction pump can be regulated or controlled until the pump comes to a stop.

The securing unit preferably forms a leaf spring clamp, wherein this leaf spring clamp anchors the pump cylinder in relation to the support unit, and wherein the leaf springs permit a pivoting movement of the cylinder.

A single leaf spring is preferably provided per cylinder. In the undeflected state, this leaf spring, or at least one of the leaf springs, preferably forms a plane in which a rectilinear continuation of said longitudinal center axis runs.

The leaf spring has a free length and a width, wherein the leaf spring is preferably made flexible in its free length. Free length is to be understood as the length between two opposite leaf spring clamps or leaf spring bearings. The ratio of free length to width is preferably less than 1. A short leaf spring of this kind permits a compact structure of the piston pump device. The thickness of the leaf spring is preferably circa 0.5 mm, its free length circa 13 mm, and its width circa 25 mm.

The leaf spring can be secured on the support unit and on the pump cylinder in a variety of ways. For this purpose, in a preferred embodiment, a first cylinder-side securing element is present which is formed in one piece with the pump cylinder or is welded onto the latter or cast therein. This ensures great stability. If the cylinder-side first securing element is also arranged in the cylinder bottom, the stability is increased still further.

In a preferred embodiment, the cylinder bottom has a substantially plane area for closing the pump cylinder, and an outwardly protruding securing seat which is formed integrally on this plane area and which serves to receive the cylinder-side first securing element.

The cylinder-side first securing element can be of different configurations and can be made of different materials. However, it is preferably block-shaped, in particular cuboid, and/or made of metal.

In a preferred embodiment, the securing unit has a cylinder-side clamping device and a support-side clamping device. The leaf spring has a first end and a second end, wherein the first end is clamped in the cylinder-side clamping device and the second end is clamped in the support-side clamping device. The cylinder-side clamping device and the support-side clamping device each have two securing elements between which the ends of the leaf spring are arranged, wherein the two elements are in each case screwed together. This arrangement too increases the stability.

If the spring is clamped at least at one end, preferably at both ends, fatigue fractures of the leaf spring can be avoided or at least minimized. Good results were obtained with block-shaped securing elements, in particular made of metal. The clamping is preferably done by means of screws, in which case the use of a torque wrench is recommended in order in turn to minimize the risk of fatigue fractures and material damage. It is also ensured that the connection does not come loose or move as a result of vibrations.

The cylinder is preferably made of polyphthalamide (PPA) or carbon-fiber-reinforced PPA. This improves the smooth running of the device and prevents squeaking The piston is also preferably made of PPA. The sealing ring of the piston is preferably made of polytetrafluoroethylene (PTFE) with carbon fibers and/or glass fibers and minerals. This leads to lubrication obtained by the first rubbing of the piston seal against the cylinder wall, made of the abovementioned materials, and in turn improves the smooth running of the device.

The piston pump device according to the invention can consist of a single cylinder/piston combination or can be assembled from several such combinations, in particular two, three, four or five such combinations. The arrangement according to the invention is suitable in particular for a reciprocating cylinder/piston pair oriented parallel to each other with two double-action cylinders and two pistons, wherein each cylinder is secured with its own securing unit and its own leaf spring on the support unit.

If a suction pump according to the invention, having a cylinder/piston pair of this kind, is provided with a single-stage gear mechanism between motor and crankshaft, the manufacturing costs can be reduced and the maintenance of the pump simplified. Moreover, the pump can be made in a compact and space-saving form. These advantages are further optimized if a toothed belt between crankshaft and motor is simply used as the gear mechanism. The toothed belt also permits operation of the pump with the least possible noise.

The two piston rods of the pistons preferably work at a 90° offset to the crankshaft.

The speed of the motor can preferably be continuously regulated. To permit simple operation, however, an adjustment and control unit is present, by means of which the motor can be adjusted to at least one or two speeds, preferably exactly three discrete speeds. This can be done in continuously regulated motors and also in other types of motors.

The piston pump device according to the invention is suitable in particular as a suction pump in the medical sector, particularly as a drainage pump for aspiration of body fluids or body fats.

BRIEF DESCRIPTION OF THE FIGURES

Preferred embodiments of the invention are described below with reference to the drawings, which serve only for explanatory purposes and are not to be interpreted as limiting the invention. In the drawings.

DETAILED DESCRIPTION

Figure 1:
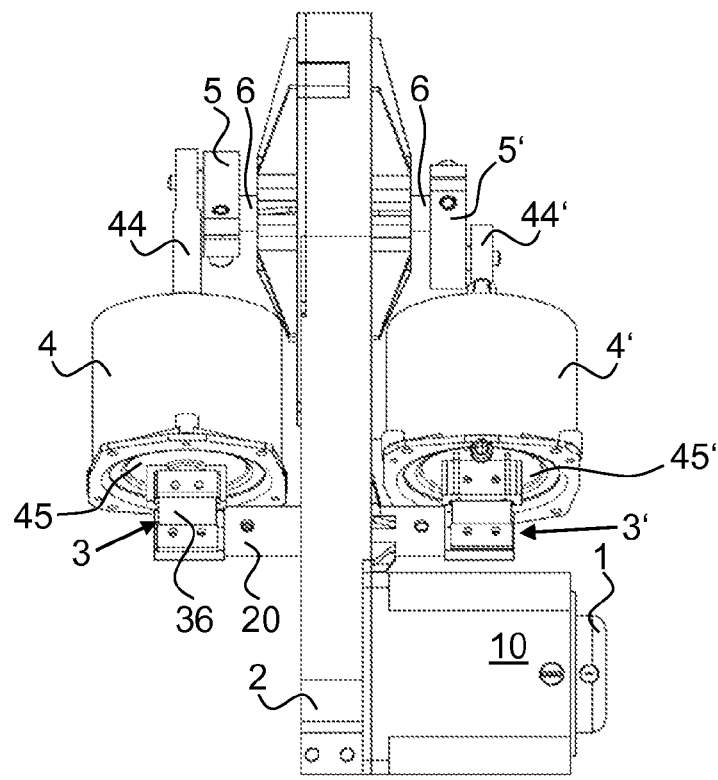
FIG. 1 shows a perspective view of a suction pump according to a first embodiment of the invention.
Figure 2:
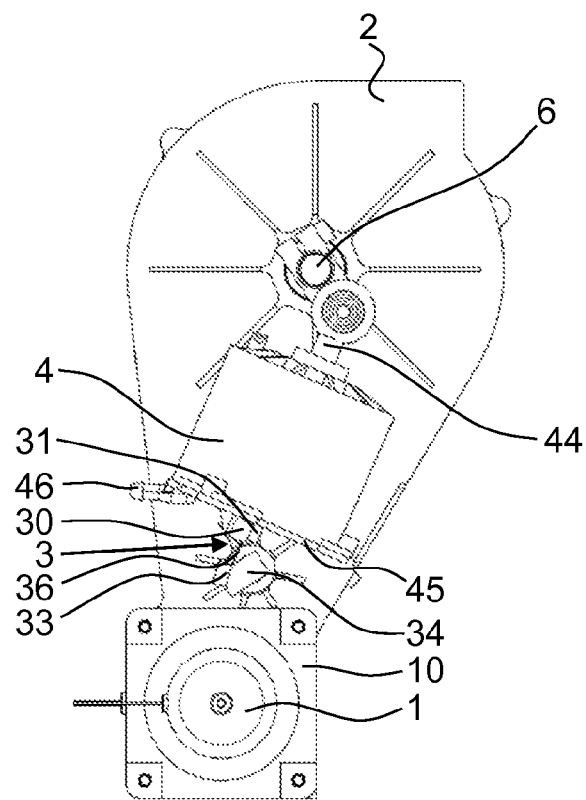
FIG. 2 shows a side view of the suction pump according to FIG. 1.

A suction pump with a piston pump device according to the invention is shown in FIGS. 1 and 2. The suction pump has an electric motor 1, which is arranged in a motor housing 10. A support unit 2 is connected to the motor housing 10. The support unit 2 encloses a toothed belt (not shown) which on the one hand is connected to a drive shaft of the motor 1 and which on the other hand drives a crankshaft 6. Instead of the toothed belt, other single-stage or multi-stage gears can also be used.

The crankshaft 6 is connected at both ends to a crank 5, 5'. Each crank 5, 5' acts on a piston rod 44, 44'. The crankshaft 6 acts at a 90° offset to the two piston rods 44, 44'. The piston rods 44, 44' are driven at an offset of 90° to each other.

The piston rods 44, 44' are parts of a piston pump device. The piston pump device has, in this example, two pump cylinders 4, 4' and, in each of these, a pump piston 42 which is arranged movably in the pump cylinder 4, 4' (see FIG. 3).

Figure 3:
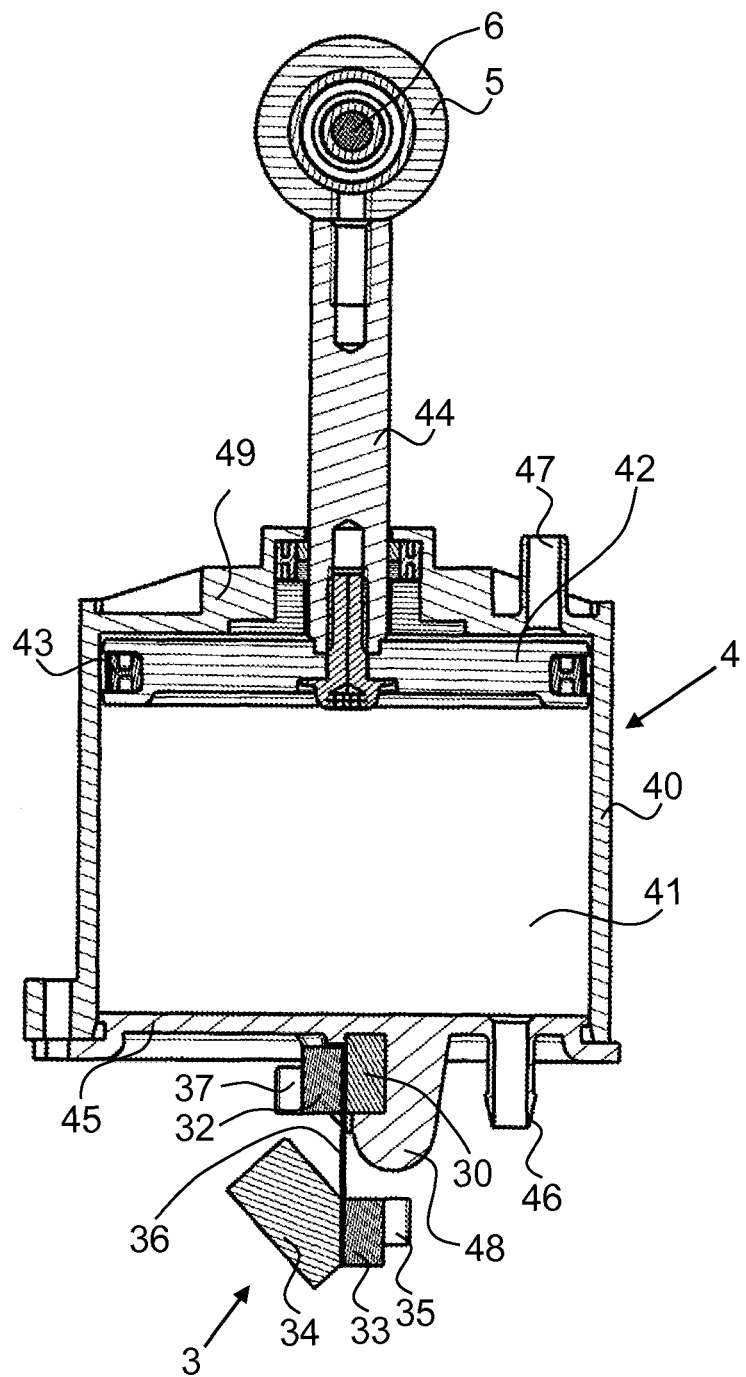
FIG. 3 shows a longitudinal section through a piston pump device according to a second embodiment of the invention.

It can be seen from FIG. 3 that the piston 42 is connected to the piston rod 44 and has a peripheral sliding seal 43. The sliding seal 43 is preferably made of polytetrafluoroethylene (PTFE), the material preferably being reinforced with carbon fibers and/or with glass fibers and minerals. The cylinder is preferably made of polyphthalamide (PPA) or of carbon-fiber-reinforced PPA. The piston is preferably made of PPA (Grivory) reinforced with glass fibers and minerals. Typical dimensions of the cylinder 4 are about 75 mm for the diameter and about 58 mm for the length.

The cylinder 4, 4' has a wall 40, a hollow space or pump chamber 41, an inlet/outlet 46 in the cylinder bottom 45, 45', and an inlet/outlet 47 in a cylinder head 49 lying opposite the cylinder bottom 45, 45'. Since the device is a double-action piston pump device, the inlets/outlets 46, 47 act as inlet or outlet depending on the direction of movement of the piston rod. The inlets/outlets 46, 47 are connected in a manner known per se to a downstream valve block (not shown).

As can be seen from FIGS. 1 and 2, the pump cylinders 4, 4' are secured on the support unit 2. For this purpose, the support unit 2 has a support arm 20, which extends transverse to the longitudinal direction of the support unit 2 and protrudes on both sides of the main body of the support. The support unit 2, with the support arm, and the motor housing are preferably made of metal or plastic.

The pump cylinders 4, 4' are each anchored on the support arm 20 via a respective securing unit 3, 3'. This anchoring is preferably effected via a cylinder bottom 45, 45'. The cylinder bottom 45, 45' is a stationary component of the pump cylinder 4, 4'. The piston 42 moves relative to the cylinder bottom 45, 45'. The cylinder bottom 45, 45' is preferably connected in a releasable manner to the rest of the cylinder by a screw connection. The corresponding screw holes are indicated by reference number 450 in FIGS. 4 and 5. The cylinder bottom 45, 45' is preferably recessed, in particular injection molded, and has a recess 451 (FIG. 5) and an elevated circumferential edge.

According to the invention, the securing unit 3, 3' comprises a leaf spring clamp with at least one, preferably exactly one, leaf spring 36. There are preferably no other bearings, in particular no sliding bearings, ball bearings or roller bearings, present between the cylinder and the support unit.

As can be seen from FIG. 3, the securing unit 3, 3' has a cylinder-side clamping device and a support-side clamping device. Both devices consist in each case of a first and a second securing element 30, 32; 34, 33. The leaf spring 36 is clamped between the respective first securing element 30, 34 and the associated second securing element 32, 33. For this purpose, screws 35, 37 are preferably present which extend through the first securing element 30, 34, the securing holes 360 of the leaf spring 36, and the second securing element 32, 33. Corresponding holes are provided for this purpose in the first securing elements 30, 34 and in the second securing elements 32, 33. Some of these holes can be seen in FIGS. 4 and 5.

The cylinder-side first securing element 30 is preferably anchored fixedly in the cylinder bottom 45. For this purpose, the cylinder bottom 45 preferably has a securing seat 48 protruding from the rest of the bottom. The seat 48 is preferably produced in one piece with the rest of the cylinder bottom, for example by injection molding. The seat 48 protrudes from the cylinder 4 at the end remote from the piston 42. The seat 48 is reinforced on one side, for example by a base that widens toward the cylinder bottom. This reinforcement is indicated by reference number 480 in FIGS. 4 to 6.

The seat 48 has a groove in which the cylinder-side first securing element 30 is secured. The securing element 30 is preferably cast into or welded into the seat or connected fixedly thereto in another way. The securing element 30 is therefore preferably connected at least with a form-fit and material fit to the cylinder, more precisely the cylinder bottom.

As can be seen from FIGS. 3 to 6, the leaf spring 36 is screwed with its cylinder-side end, together with the cylinder-side second securing element 32, onto the cylinder-side first securing element 30. The same happens with the second support-side end of the leaf spring 36. The support-side first securing element 34 and the associated second securing element 33 can be seen in FIG. 3. The support-side first securing element 34 is secured on the support arm 20 in a similar way or in the same way as its counterpart is secured on the cylinder bottom 45. Here too, the support arm 20 is preferably provided with a reinforced seat for a form-fit and material fit connection to the support-side first securing element 34. The seat can also be produced in one piece with the support arm 20 or can at least be welded to the latter.

Figure 4:
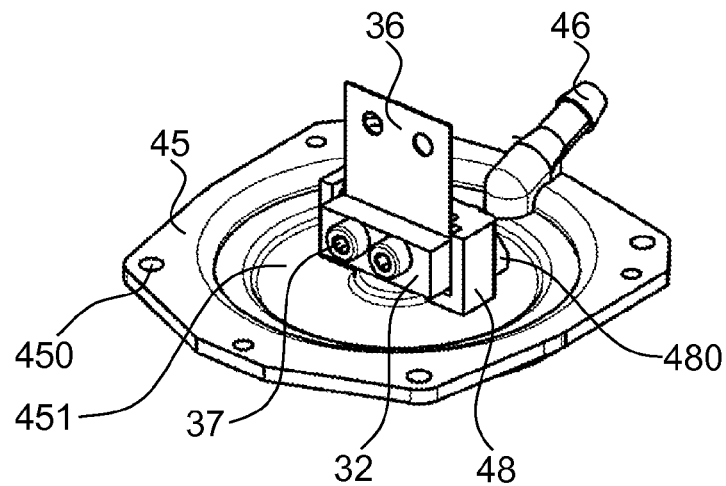
FIG. 4 shows a perspective view of a cylinder bottom with cylinder-side securing part and leaf spring according to the suction pump shown in FIG. 1.
Figure 5:
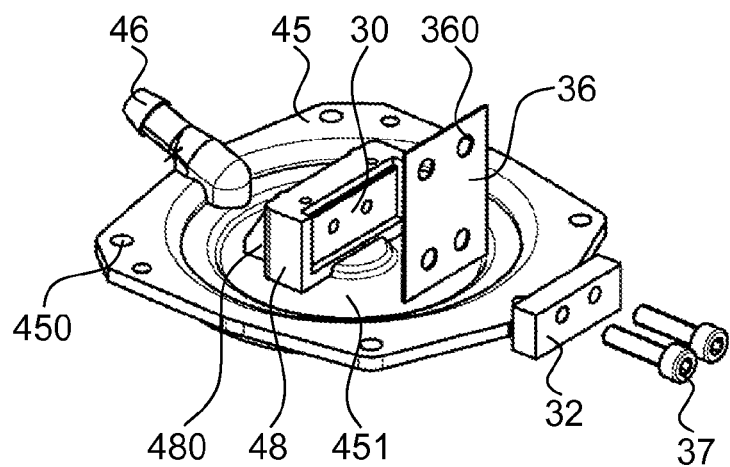
FIG. 5 shows an exploded view of the cylinder bottom according to FIG. 4 with cylinder-side securing part and leaf spring.
Figure 6:
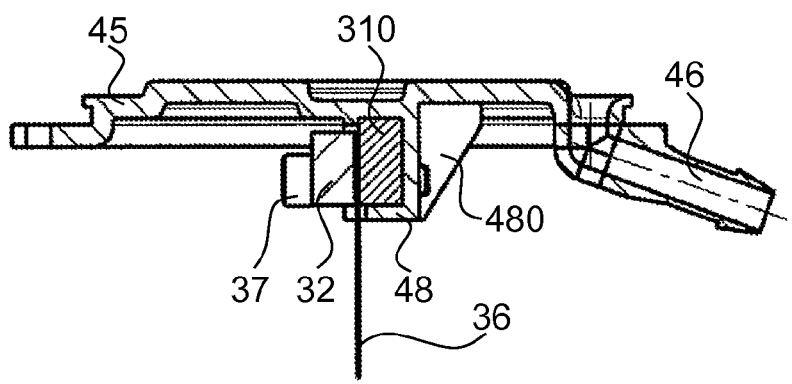
FIG. 6 shows a cross section through the cylinder bottom according to FIG. 4.

The embodiment according to FIG. 3, on the one hand, and the embodiments according to FIGS. 4 to 6, on the other hand, differ particularly in terms of the design of the cylinder bottom 45, particularly the inlet 46, and the shape of the seat 48. Other shapes are possible.

Preferably, at least the cylinder-side first securing element 30 is made of metal. It is preferably block-shaped or cuboid. The support-side first securing element 34 is preferably also made in this shape and from metal. In a preferred embodiment, the second securing elements 32, 33 are also designed in this way.

The leaf spring 36 is short. The free length of the leaf spring 36 between the clamps is preferably less than the width. Preferably, the length is at least not substantially greater than the width. Typical measurements for free length, width and thickness are circa 13 mm, 25 mm and 0.5 mm.

As can be seen from FIGS. 3 and 6, the leaf spring 36 extends substantially in a plane in which the longitudinal center axis of the cylinder 4 also extends. During operation, the cylinder 4, 4', by virtue of the leaf spring 36, is now able to execute a pivoting movement relative to the direction of movement of the piston 42. This applies equally to both cylinders 4, 4', since the securing device of the second cylinder 4' is identical to that of the first cylinder 4.

This arrangement can also be provided in other piston pumps. However, the suction pump shown here has further advantageous features which can also be used independently of the above-described securing device according to the invention. The motor 1 can be actuated via an adjustment and control unit (not shown here). The adjustment and control unit has in particular at least one adjustment possibility, preferably three discrete adjustment possibilities, for the operation of the motor. These are, for example, three buttons, or a switch with three operating positions. For reasons of hygiene, capacitive sensors, particularly with three operating positions, can also be used for this purpose. The switch can also have an off position. These three operating positions each select a discrete motor speed and, therefore, three discrete suction capacities of the pump, for example 40 l/min, 50 l/min and 60 l/min. The mean suction capacity preferably corresponds to a normal operating state or a recommended operating state. It is in this way possible to simplify the operation of the pump, even when a motor is used which in principle is steplessly adjustable.

The piston pump device according to the invention is wear-resistant and runs quietly. When used as a suction pump, it additionally permits a controllable air flow until the pump comes to a stop.

The invention claimed is:

1. A piston pump device with a support unit, a pump cylinder, and a pump piston arranged in the pump cylinder, the pump cylinder having a longitudinal center axis, and a cylinder bottom arranged perpendicular to the longitudinal center axis, the pump piston being movable relative to the cylinder bottom, and the pump cylinder being secured on the support unit by a securing unit, wherein the securing unit has a leaf spring, which permits a pivoting movement of the longitudinal center axis of the pump cylinder relative to the support unit, wherein the securing unit has a cylinder-side clamping device and a support-side clamping device, wherein the leaf spring has a first end and a second end, and wherein the first end is clamped in the cylinder-side clamping device and the second end is clamped in the support-side clamping device.

2. The piston pump device as claimed in claim 1, wherein the securing unit is secured on the cylinder bottom.

3. The piston pump device as claimed in claim 1, wherein the securing unit forms a leaf spring clamp, and wherein the leaf spring clamp anchors the pump cylinder in relation to the support unit.

4. The piston pump device as claimed in claim 1, wherein the leaf spring in the undeflected state forms a plane, and wherein a rectilinear continuation of said longitudinal center axis runs in the plane.

5. The piston pump device as claimed in claim 1, wherein the leaf spring has a free length and a width, wherein the leaf spring is made flexible in its free length, and wherein the ratio of free length to width is less than 1.

6. The piston pump device as claimed in claim 1, wherein the securing unit has a single leaf spring.

7. The piston pump device as claimed in claim 1, further comprising a cylinder-side first securing element formed in one piece with the pump cylinder or welded onto the pump cylinder, or cast therein.

8. The piston pump device as claimed in claim 7, wherein the cylinder-side first securing element is arranged in the cylinder bottom.

9. The piston pump device as claimed in claim 8, wherein the cylinder bottom has a substantially plane area for closing the pump cylinder, and an outwardly protruding securing seat which is formed integrally on the plane area and which serves to receive the cylinder-side first securing element.

10. The piston pump device as claimed in claim 7, wherein the cylinder-side first securing element is a block-shaped metal piece.

11. The piston pump device as claimed in claim 1, wherein the cylinder-side clamping device and the support-side clamping device each have a first and a second securing element, wherein the leaf spring is clamped at the first end and the second end, two ends between the securing elements, and wherein a first and a second of the securing elements are in each case screwed together.

12. The piston pump device as claimed in claim 1, further comprising two pairs consisting of a pump cylinder, a piston and a securing unit, and wherein the longitudinal center axes of the pump cylinders extend parallel to each other in the undeflected state of the pump cylinders.

13. A suction pump comprising:
a piston pump device having a support unit;
a pump cylinder having a longitudinal center axis and a cylinder bottom arranged perpendicular to the longitudinal center axis;
a pump piston arranged in the pump cylinder, the piston being moveable relative to the cylinder bottom;
a securing unit for securing the pump cylinder on the support unit;
a crankshaft for moving the pump piston;
a motor for driving the crankshaft; and
a gear mechanism connecting the motor and the crankshaft, the gear mechanism being a sing-stage gear;
wherein the securing unit has a leaf spring which permits a pivoting movement of the longitudinal center axis of the pump cylinder relative to the support unit, wherein the securing unit has a cylinder-side clamping device and a support-side clamping device, wherein the lead spring has a first end and a second end, and wherein the first end is clamped in the cylinder-side clamping device and the second end is clamped in the support-side clamping device.

14. The suction pump as claimed in claim 13, wherein an adjustment and control unit is present, by means of which the motor is adjustable to at least one speed.

15. The suction pump as claimed in claim 14 wherein the motor is adjustable to exactly three discrete speeds.

16. A piston pump device with a support unit, a pump cylinder, and a pump piston arranged in the pump cylinder, the pump cylinder having a longitudinal center axis, and a cylinder bottom arranged perpendicular to the longitudinal center axis, the pump piston being movable relative to the cylinder bottom, and the pump cylinder being secured on the support unit by a securing unit, wherein the securing unit has a leaf spring, which permits a pivoting movement of the longitudinal center axis of the pump cylinder relative to the support unit, the piston pump device further comprising a cylinder-side first securing element formed in one piece with the pump cylinder or welded onto the pump cylinder, or cast therein, and wherein the cylinder-side first securing element is a block-shaped metal piece.

17. A piston pump device with a support unit, a pump cylinder, and a pump piston arranged in the pump cylinder, the pump cylinder having a longitudinal center axis, and a cylinder bottom arranged perpendicular to the longitudinal center axis, the pump piston being movable relative to the cylinder bottom, and the pump cylinder being secured on the support unit by a securing unit, wherein the securing unit has a leaf spring, which permits a pivoting movement of the longitudinal center axis of the pump cylinder relative to the support unit, the piston pump device further comprising two pairs consisting of a pump cylinder a piston and a securing unit, and wherein the longitudinal center axis of the pump cylinder extend parallel to each other in the undeflected state of the pump cylinders.

* * * * *